United States Patent [19]

Peer

[11] 4,432,998
[45] * Feb. 21, 1984

[54] PREPARATION OF BACTERIA CULTURES TOLERANT TO METAL IONS

[75] Inventor: Herbert R. Peer, Storm Lake, Iowa

[73] Assignee: Transagra Corporation, Storm Lake, Iowa

[ * ] Notice: The portion of the term of this patent subsequent to Sep. 14, 1999 has been disclaimed.

[21] Appl. No.: 414,817

[22] Filed: Sep. 3, 1982

Related U.S. Application Data

[63] Continuation-in-part of Ser. No. 873,156, Jan. 27, 1978, Pat. No. 4,349,569; which is a continuation of Ser. No. 711,454, Aug. 4, 1976, abandoned.

[51] Int. Cl.³ .................. A23C 9/12; C12N 1/36; C12N 1/20; C12R 1/23
[52] U.S. Cl. ................... 426/43; 426/34; 426/807; 435/245; 435/253; 435/853; 435/854; 435/857; 435/885
[58] Field of Search .............. 426/34, 36, 39, 41, 426/43, 61, 807; 435/253, 853, 854, 245, 857, 435/885

[56] References Cited

U.S. PATENT DOCUMENTS

| | | | |
|---|---|---|---|
| 3,343,962 | 9/1967 | Peer | 435/253 X |
| 3,354,049 | 11/1967 | Christensen | 426/39 X |
| 3,497,359 | 2/1970 | Peer | 435/61 |
| 3,843,801 | 10/1974 | Efthymiou | 426/36 |
| 3,900,572 | 8/1975 | Peer | 426/43 X |
| 3,914,438 | 10/1975 | Holt et al. | 426/41 X |
| 4,020,185 | 4/1977 | Andersen et al. | 426/36 |
| 4,349,569 | 9/1982 | Peer | 426/43 |

OTHER PUBLICATIONS

Webb et al., By Products From Milk, 2nd Ed. The Avi Publishing Co., Inc., Westport, Conn. 1970 (pp. 24–29, 32 & 33).
Manual For Dairy Manufacturing Short Courses, Kurtz Bros., Clearfield, Pa. 1956 (pp. 56–57 ).

*Primary Examiner*—David M. Naff
*Attorney, Agent, or Firm*—Laurence R. Brown

[57] ABSTRACT

Lactobacillus and Streptococcus are cultured by special process steps to derive by controlled transmutation a strain of organisms having high tolerance to acidity above 1.5%, and are tolerant to metallic salts such as cobalt carbonate which tend to poison such organisms by limiting growth. The organisms are cultured in a transfer process from starter organisms that tend to clump in the presence of metallic ions to develop the improved strain which does not clump when cultured in the presence of metallic salts thereby permitting increased production. A characterizing feature of the resulting transmuted organisms therefore is the freedom of a tendency to clump in the presence of the cobalt ion, a feature uncharacteristic of the starting organisms. The organisms are useful for enhancing animal and plant growth.

9 Claims, 2 Drawing Figures

PREPARATION OF BACTERIA CULTURES TOLERANT TO METAL IONS

BACKGROUND OF THE INVENTION

This application is a continuation-in-part of the application U.S. Ser. No. 873,156 filed Jan. 27, 1978 U.S. Pat. No. 4,349,569-Sept. 14, 1982) which was a continuation of Ser. No. 711,454 filed Aug. 4, 1976, now abandoned, for "Improved Culture of *Lactobacillus Acidophilus*".

TECHNICAL FIELD

This invention relates to the culture of organisms enhancing living animal and plant culture, e.g. Lactobacillus and Streptococcus which are cultured in the presence of metal ions such as cobalt salts, and more particularly it relates to such culture which makes the organisms tolerant to the presence of metallic salts such as cobalt carbonate which act with a poisoning effect on the organisms.

In the production of cultured whey products such as described in my U.S. Pat. Nos. 3,343,962-Sept. 26, 1967 and 3,497,359-Feb. 24, 1970 a mother culture is produced by culturing *Lactobacillus acidophilus* in a milk nutrient base in the presence of cobalt carbonate. This conditions the organisms to become tolerant to a higher acidity condition than usually expected from *Lactobacillus acidophilus*, a desirable characteristic.

It has now been found, however, that at least some Lactobacillus and Streptococcus strains are sensitive to addition of metallic ions such as obtained in the presence of cobalt carbonate, a phenomenon that may be termed metal poisoning. This is evidenced by acidity significantly lower than 1.3%, dwarfing to lengths of three microns or less and clumping of the organisms in the presence of cobalt carbonate.

Usual strains of Lactobacillus and Streptococcus can be expected to have a percent of acidity, expressed as Lactic acid, below 1%. The desired strains tolerant to metal ions therefore more readily produce a desired acidity in the order of 1.3% or greater.

The organism physical characteristics of a typical laboratory strain of *Lactobacillus acidophilus* show a size of three to five microns with thin rod-like structure, some bent and L-shaped and with a more or less loosely held, almost transparent outer sheath that tends to collapse and wrinkle. As shown in the parent patent, *Lactobacillus acidophilus* organisms are increased in size and toughness by a series of culture steps which transmute the starting strain.

It has been shown in U.S. Pat. No. 3,914,438 issued to Lemmie C. Holt-Oct. 21, 1975 that nutrient compositions of organisms cultured in whey to produce a lactic acid fermentation product including *Lactobacillus acidophilus* and *bulgaricus* enhance living plant and animal growth.

It is also shown in the "Manual for Dairy Manufacturing", Kurtz Bros., Clearfield, Pa. 19562, page 56, that the Streptococcus organism similarly reacts in fermenting whey.

It has also been observed by applicant, as evidenced in the parent patent, that some strains of organisms that enhance living plant and animal culture including Lactobacillus and Streptococcus tend to clump or cluster together when in the presence of metallic ions such as cobalt carbonate. Thus they cannot produce efficiently in fermentation or culture steps because they starve each other by preventing access to the nutrient solutions in which they are fermented.

Other equivalent metallic ions such as manganese, nickel or zinc may be used in the culture of the organisms to introduce desired trace metals into the produced product as set forth in my copending application Ser. No. 111,023 filed Jan. 10, 1980, now abandoned., a continuation of Ser. No. 875,754 filed Feb. 7, 1978 abandoned, which is incorporated herein in its entirety by reference. The organisms involved in this application are sensitive to this range of metsl ions, which tends to cause clumping and reduced production in manufacture. Thus, reduction of sensitivity to cobalt and other metallic ions is a limiting problem in the art.

A problem is presented when trying to preserve live organisms for use in the culture of plants and animals, since storage conditions become stringent and the live organism count is critical to performance. The hereinbefore mentioned Peer patents show that the *Lactobacillus acidophilus* organisms can be made non-viable at the end of the fermenting or culture cycle for example by adding high concentrations of Lactic acid, and thus can be stored non-critically for later use for plant and animal culture.

OBJECTS OF THE INVENTION

It is therefore a general object of this invention to develop strains of organisms that enhance living plant and animal culture that are more readily manufactured, are tolerant of higher acidity levels, produce higher yields and are more tolerant to the presence of metallic ions.

A more specific object of the invention is to produce transmuted organism strains more tolerant in the culturing stage of lactic acid, which is a self-limiting product of the culture that controls the yield of cultured organisms, and which produce more lactic acid in the presence of metallic ions.

Another object of the invention is to produce organism strains identified by the characteristic that they do not clump together in the presence of metallic ions, thereby improving production and capacity to produce lactic acid.

A still further object of the invention is to produce organism strains treated with metallic ions such as cobalt carbonate that are identified by the characteristic that they retain their cell structure and their propensity to enhance living plant and animal culture when converted to non-viable form.

BRIEF DESCRIPTION OF THE INVENTION

Therefore, in accordance with this invention a starter strain of metal ion sensitive organisms with a propensity to clump or cluster in the presence of the metal ion is cultured and transmuted into a substantially cluster free hardier strain of organisms tolerant to higher acidity and the presence of metal ions which enables the organisms to have the property of enhancing living plant and animal culture and which therefore can be produced more efficiently.

The culture process comprises a series of culture transfers where the organisms are cultured in a culture medium such as milk, corn steep liquor or the like, in the presence of a low concentration of metallic ion such as cobalt with the presence of an ammonium compound. This transfer is enabled by a controlled transmutation process to transmute the organisms into a strain that withstands higher acid and metallic ion concentrations and to exhibit better physical characteristics and more efficient yields from culture or fermentation.

In order to declump the organisms in the presence of metallic ions such as cobalt carbonate, the organisms are sub-cultured several times through fresh medium having present therein an ammonium ion in the presence of the metallic ion, such as in a skim milk medium with a cobalt carbonate equivalent of 0.001% to 0.03% in cobaltous ammonium lactate. Thereafter strains of non-clumping acid resistant organisms are developed that retain the desirable characteristics of enhancing plant and animal culture in the non-viable state, and have the characteristic of producing more rapidly in fermentation because the clumping does not interfere with nutrition. Ammonium ion is the important constituent in the reagent complex and could be supplied by any number of ammonium compounds. For example; ammonium lactate, ammonium acid phosphate, ammonium chloride, ammonium citrate, ammonium tartrate, ammonium carbonate and the ammonium salts of certain free amino acids.

THE DRAWING

FIGS. 1 and 2 respectively are comparative microphotographs at 500 times magnification showing organisms which clump and those which are free from clumping as related to the present invention.

DETAILED DESCRIPTION OF THE INVENTION

The general process of transfer through a series of fermenting cycles of a starter culture stock treated with a metallic ion such as cobalt carbonate with a Lactobacillus strain is set forth in the before mentioned U.S. Patents. A starting commercial source of *Lactobacillus acidophilus*, for example, can be obtained from Chr. Hansen's Lab. Inc., Milwaukee, Wisc. in freeze-dried powder form. The currently available strain is described in the "American Cultured Dairy Products Journal", Vol. 10, No. 1, Feb. 1975 in a study by E. M. Mikolojcik and I. Y. Hamdon. Also it is known that mother cultures are preserved by storage at 4° C.

Cultures of Lactobacillus and Streptococcus exhibiting the characteristic of enhancing living animal and plant culture in the non-viable state, as used in the examples set forth herein were obtained from the American Type Culture Collection (ATCC) or Northern Regional Research Lab (NRRL). Cultures *Lactobacillus bulgaricus* ATCC No. 11842 and cultures *Lactobacillus casei* ATCC No. 7469, *Lactobacillus plantarum* ATCC No. 8014, *Lactobacillus acidophilus NRRL No. B*-3208 and *Streptococcus faecium* ATCC No. 19434 received in our laboratory in a freeze-dried form were opened and placed in skim milk which had been treated by heating at 5–15 pounds PSIG steam for ten to twenty minutes. The cultures were incubated at approximately 33°–37° C. for 24 to 72 hours.

After culture growth developed, as observed by milk clotting and microscopic observation of cellular growth, the cultures were stored in a refrigerator (4° C.) until needed. Viability of each culture was retained by monthly subculturing the organism in skim milk (heat treated as above) at 33°–37° C. for 24 to 72 hours and again storing in a refrigerator until needed.

Figure 1:
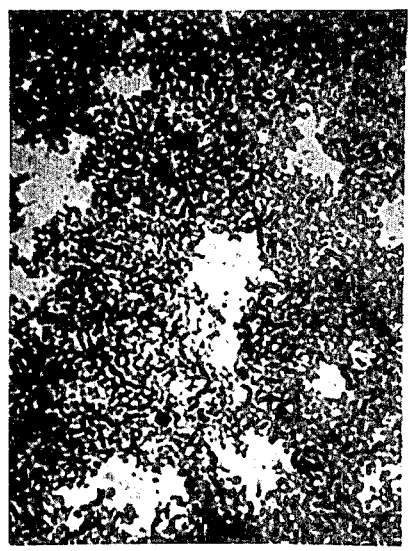

Observation under a microscope of oraganisms sub-cultured in the presence of the metallic ion such as the cobalt carbonate prestarter and starter procedures of my U.S. Pat. No. 3,497,359 will show the organisms are clumped together when viewed in a distlled water suspension dilution of 50 to one as shown in FIG. 1, for example. To observe densities, samples may be brought to 0.1% acidity with addition to NaOH solution which releases the clumping. The tendency of the organisms is to clump at higher acidity. The organisms are small in the order of three to five microns in length with many curved and L-shaped forms. The percentage of acidity is low of the order of 1.2%, and below.

Figure 2:
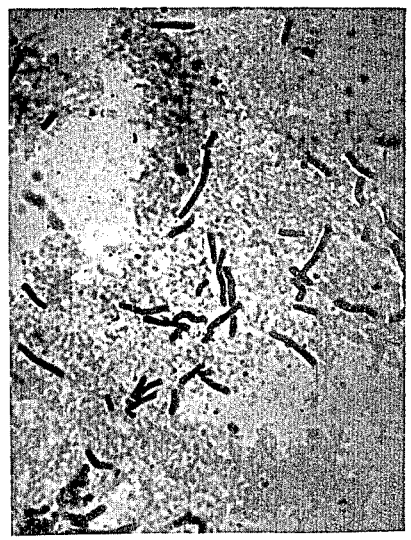

In accordance with this invention by means of serial transfer through a number of sub-culture cycles with a fresh medium containing the metal ion and an ammonium ion, the clumping characteristic disappears as shown in FIG. 2 of the drawing.

In summary:

when the samples are cultured in the presence of 100 to 500 ppm of cobalt carbonate added to the milk before autoclaving, the acidity does not rise, the organisms are retarded in growth and the clumping condition persists through many transfers. Also the condition persists even when the cobalt carbonate is withdrawn through a further series of transfers. It is thus evident that the cobalt carbonate has a restraining effect on the development of the initial small size, low acid transfer of organisms which becomes fixed by some unknown conditioning mechanism.

In order to provide a non-clumping organism for use in the presence of cobalt carbonate or like metal salts it has been found in accordance with this invention that the characteristics of the organism become transmuted without the clumping characteristic when the starter strains are developed in a series of culture steps with fresh or new medium containing both the metal ion and an ammonium ion.

It is thought that the initial presence of free cobalt ion (100 ppm or above) during early development of acidity, in some way inhibits the respiratory function.

That is, as the acidity values increase from 0 to 1.2% (in the presence of cobalt ion), the clumping phenomenon progressively increases until it becomes total, and further acid production is thus diminished.

The introduction of ammonium ion (ammonium lactate) in some way masks the cobalt ion so that clumping is avoided, presumably thru the formation of some coordination complex such as $Co(NH_3)_6^{++}$ or $Co(NH_3)_6^{+3}$ [Hexammonium II or III].

It is deduced that the initial laboratory strain is an organism specially adapted for use in milk products, and that it provides new strains having distinctive properties retained after development by transmutation in a serial transfer process.

Treatment by a metal salt tends to permanently change organism characteristics which otherwise reverts in the serial transfer process of the sub-culture process afforded this invention for that class of organisms which in the non-viable stabilized state enhance living animal and plant culture as cultured in various media and in the presence of various metal ions and conditions exemplified by the ensuing examples. As set forth in my U.S. Pat. No. 3,497,359, the end product is stabilized in its non-viable state by a large dose (10 to 12%) of lactic acid in the final processing stages.

The general process for producing improved non-clumping, acid resistant organisms required that the organism be sub-cultured several times through fresh or new medium prepared as follows:

Flask I: skim milk or other medium

Flask II: skim milk or other medium+0.001% to 0.3% cobalt carbonate

Flask III: skim milk or other medium+cobalt carbonate equivalent 0.001% to 0.03% in cobaltous ammonium lactate The ammonium lactate may be prepared by treating 100 ml tech lactic acid (88%) with 26° BE' ammonium hydroxide until the mixture is slightly basic and driving off excess ammonia by gentle heat reducing the volume of the reaction by evaporation to 100 ml. The chemical process is expressed as

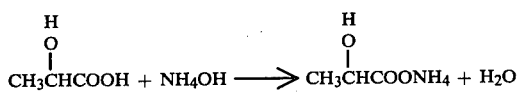

The first transfer of this example shows a positive shift to the larger forms of the improved strain free of clumping. However, this strain exhibits acidity of a lower range less than 1.5%.

The cobaltous ammonium lactate reagent is prepared as follows:

1. Construct a 15 to 20% Aq. solution of ammonium lactate (by weight).
2. Add 0.010 grams cobalt carbonate per milliliter of ammonium lactate solution.
3. Agitate solution frequently at room temperature (25° C.) until a clear, red solution results.

250 ml flasks were filled with 100 ml of the above medium. The cotton plugged flasks were autoclaved at 5-15 PSIG for 10-20 minutes, cooled to incubation temperatures and inoculated with 1-15 ml of the desired culture. The flasks were incubated at 33°-37° C. for 24 to 72 hours in a stationary condition until growth has developed. The flasks were then placed in a refrigerator for 24-72 hours. Each flask is then brought out of the refrigerator and the culture used to inoculate a flask of fresh, autoclaved identical medium. The inoculum represents 1-15% (volume/volume) of the original medium. The above serial sub-culturing process is repeated until culture declumping is complete, increased organism population and acid production is increased.

Acid production, organism population count and degree of declumping are recorded throughout the serial transfer process. The acid production is determined by titration of the acid in the culture with standard sodium hydroxide. The organism population count and clumping is determined by diluting the culture in water and placing the diluted culture sample on a bacterial counting chamber and observing the sample at 450×magnification. The amount of clumping was determined by counting the organism first in (a) acid (normal medium pH) water dilutions and then (b) base water dilutions. The normally acid dilution water above is adjusted to a basic condition (pH 8.0) with sodium hydroxide. The organism disperses or declumps under basic conditions. The difference in count between (a) acid condition and (b) basic conditions was used as an index of clumping in the culture.

EXAMPLE 1

Here the 150 ml skim milk was treated with 25 ppm cobalt carbonate and 2 grams ammonium lactate before autoclaving at 5 psi for 20 minutes. The cooled milk at 37° to 38° C. was inoculated with 0.5 gram of the dried commercial "Lactobacillus acidophilus and incubated at that temperature for 24 hours.

This starting sub-culture without further transfer is unique in exhibiting large organisms (30% at 15 microns) and is only partially clumped with an organism density of 450 million/ml and acidity of 1.6%.

With high concentrations of cobalt carbonate above 100 ppm there is a tendency to intimidate transmutation, particularly in the absence of an ammonium compound. It is noted the total organism protoplasm is increased with larger organisms and therefore and density count may decrease.

On the second serial transfer under the same conditions and culture is free of clumping and acidity rises sharply to the order of 2.5% and very large cells are observed (20 to 25 microns).

In the third transfer even with addition of more cobalt carbonate (100 ppm) and 1.5 grams ammonium lactate the number of organisms and acidity improves (1.7 billion and 2.7%). Thus, an improved strain of organisms is developed by initial treatment in the presence of an ammonium source, which strain is not intimated or retarded in the presence of cobalt carbonate.

In this example it is observable that the presence of a base substance such as ammonium is a factor in avoidance of clumping and in the development of an improved organism strain.

This series maintains the organism properties over the serial transfer process in the presence of 100 ppm of cobalt carbonate and 1 gram of ammonium lactate for 150 ml milk.

EXAMPLE 2

Those skilled in the art can choose alternative nitrients such as tomato juice or those listed in subsequent examples, and alternative metal salts including compounds preferably carbonates or iron, manganese, nickel, chromium, zinc, cadmium, copper, molybdenum and vanadium in the same procedure. All these metals have orbital electron patterns that permit them to form complexes with ammonium ion.

To better illustrate the development of the desired non-clumping characteristic under typical conditions with the specified class of organisms, the following examples are related to the foregoing ingredients identified by Flask I, II, III nomenclature.

Flasks I and II described above function as clumping controls for the Flask III. Cultures grown under Flask I conditions do not clump. Cultures grown under Flask II conditions produce clumped cultures. Cultures grown under Flask III conditions do not clump.

EXAMPLE 3

In this example Lactobacillus acidophilus strain NRRL B-3208 was serially transferred in a medium containing principle nutrients of dextrose and corn steep liquor. The medium was prepared by first centrifuging or filtering out all corn steep liquid particulate material. The soluble fraction of the corn steep liquor was then added to dilution water for medium preparation. The first of three sets of flasks (I) contained no cobalt. The second set of flasks (II) contained 0.001% to 0.03% cobalt carbonate added to the medium prior to autoclaving. The third set of flasks (III) contained 0.001% to 0.03% cobalt carbonate equivalent in cobaltous ammonium lactate, also added to the medium prior to autoclaving. The final medium containing five percent dextrose (weight/volume) and two percent dry substance (weight/volume) corn steep liquor was pH adjusted to 6.0 with sodium hydroxide. The medium was autoclaved at fifteen pounds per square inch steam pressure for fifteen minutes. After the medium had cooled to incubation temperatures 33°–37° C., it was inoculated with 5% volume of inoculum to volume of medium Lactobacillus acidophilus NRRL B-3208. The flasks of cultures were incubated in a stationary condition at 37° C. for 72 hours. The cultures were then placed in a refrigerator for 72 hours. After being refrigerated, the cultures were taken from the refrigerator and inoculated into fresh medium of identical composition above. Results of the culture growth are given in Table 1.

TABLE 1

Growth of Lactobacillus acidophilus NRRL B-3208 in Cobalt Free Medium Containing Corn Steep Liquor and Dextrose.

| Number of Serial Transfers | Titratable Acid (%) | Cell Count Acid Dilutions | Cell Count Base Dilutions | Amount (%) Declumping |
|---|---|---|---|---|
| 1 | 0.8 | 20 | 21 | 5 |
| 2 | 0.9 | 20 | 23 | 15 |
| 3 | 1.0 | 21 | 26 | 24 |
| 4 | 1.0 | 29 | 29 | 0 |
| 5 | 1.1 | 31 | 45 | 45 |

TABLE 2

Growth of Lactobacillus acidophilus B-3208 in Cobalt Carbonate Corn Steep Liquor and Dextrose.

| Number of Serial Transfers | Titratable Acid (%) | Cell Count Acid Dilutions | Cell Count Base Dilutions | Amount (%) Declumping |
|---|---|---|---|---|
| 1 | 0.9 | 20 | 21 | 5 |
| 2 | 1.0 | 24 | 45 | 88 |
| 3 | 1.0 | 23 | 47 | 104 |
| 4 | 1.3 | 36 | 151 | 219 |
| 5 | 1.4 | 43 | 179 | 216 |

These data show the clumping characteristic effected by sub-culturing in the presence of the metallic ion.

TABLE 3

Growth of Lactobacillus acidophilus NRRL B-3208 in Cobaltous Ammonium Lactate Corn Steep Liquor and Dextrose Medium.

| Number of Serial Transfers | Titratable Acidity (%) | Cell Count Acid Dilutions | Cell Count Base Dilutions | Amount (%) Declumping |
|---|---|---|---|---|
| 1 | 0.9 | 24 | 25 | 4 |
| 2 | 1.0 | 28 | 29 | 4 |
| 3 | 1.3 | 35 | 38 | 9 |
| 4 | 1.6 | 63 | 69 | 10 |
| 5 | 1.8 | 100 | 110 | 10 |

Analysis of the results show that the presence of cobalt carbonate increased the cell population (organisms/milliliter) and acidity. Severe organism clumping was eliminated when the acidic dilution water was made basic and organism population counted again. The clumping was evident by the large difference in cell population between the acidic and basic dilution water. The success of cobaltous ammonium lactate in preventing clumping but allowing for higher organism population and acidity is shown by comparison of Tables 1 and 2 with Table 3. In Table 3 the cell population and acidity is higher than those found in Tables 1 and 2. The stimulation of increased production of cell population and acidity by cobalt and the cellular declumping in the presence of cobaltous ammonium lactate is shown in subsequent examples using other Lactobacillus and Streptococcus organisms in media other than that above.

EXAMPLE 4

In this example, Lactobacillus bulgaricus ATCC strain No. 11842 was used. The culture medium containing skim milk was prepared in three categories, this is (1) no cobalt, (2) 0.001%–0.03% cobalt carbonate, and (3) 0.001%–0.03% cobalt carbonate equivalent in cobaltous ammonium lactate. The cobalt was added prior to autoclaving. The culture medium pH was "as is" or that found in milk, pH 6–6.3. The autoclaving, inoculation and serial transfer culturing were carried out as given in Example 1. Typical results are given in the following tables.

TABLE 1

Growth of Lactobacillus bulgaricus ATCC 11842 in Cobalt Free Skim Milk Medium.

| Number of Serial Transfers | Titratable Acidity (%) | Cell Count Acid Dilutions | Cell Count Base Dilutions | Amount (%) Declumping |
|---|---|---|---|---|
| 1 | 0.9 | 18 | 19 | 5.5 |
| 2 | 1.1 | 19 | 19 | 0 |
| 3 | 1.1 | 19 | 19 | 0 |
| 4 | 1.2 | 20 | 30 | 50 |
| 5 | 1.3 | 30 | 84 | 180 |

TABLE 2

Growth of Lactobacillus bulgaricus ATCC 11842 in Cobalt Carbonate Skim Milk Medium.

| Number of Serial Transfers | Titratable Acidity (%) | Cell Count Acid Dilutions | Cell Count Base Dilutions | Amount (%) Declumping |
|---|---|---|---|---|
| 1 | 1.0 | 16 | 16 | 0 |
| 2 | 1.4 | 18 | 18 | 0 |
| 3 | 1.5 | 18 | 100 | 255 |
| 4 | 1.8 | 19 | 194 | 521 |
| 5 | 1.9 | 19 | 1000 | 2631 |

TABLE 3

Growth of Lactobacillus bulgaricus ATCC 11842 in Cobaltous Ammonium Lactate Skim Milk Medium.

| Number of Serial Transfers | Titratable Acidity (%) | Cell Count Acid Dilutions | Cell Count Base Dilutions | Amount (%) Declumping |
|---|---|---|---|---|
| 1 | 1.3 | 18 | 18 | 0 |
| 2 | 1.3 | 22 | 26 | 18 |
| 3 | 1.4 | 106 | 120 | 13 |
| 4 | 1.8 | 144 | 152 | 6 |
| 5 | 1.9 | 144 | 186 | 29 |

EXAMPLE 5

In this example Lactobacillus casei ATCC strain No. 7469 was used. The culture medium was comprised of skim milk and either cobalt carbonate or cobaltous ammonium lactate. If cobalt was present it was added prior to autoclaving. These experiments on cobalt were set up according to the procedure given in Example 1. Results of the work shows that the presence of cobalt increases cell count and acidity but clumps the culture. Further growth in cobaltous ammonium lactate declumps the culture while retaining high acidity and cell count population.

EXAMPLE 6

In this example Lactobacillus plantarum ATCC strain No. 8014 was used. The culture medium used in this example was corn steep liquor, dextrose and either cobalt carbonate or cobaltous ammonium lactate. The culture medium preparation, inoculation and cultivation was conducted as described in Example 1. Typical results similar to *Lactobacillus acidophilus* and *Lactobacillus bulgaricus* are produced here and are not limited to the amounts of cobalt used here.

EXAMPLE 7

In this example *Lactobacillus plantarum* ATCC strain No. 8014 was used. The culture medium used in this example was skim milk and either cobalt carbonate or cobaltous ammonium lactate. Preparation of the milk medium was done as described in Example 2. Serial transfer culturing was carried out as described in Example 1. Typical and similar response to cobalt are shown in this example. The responses are not limited to only these cobalt concentrations.

EXAMPLE 8

In this example *Streptococcus feacium* ATCC strain No. 19434 was used. The culture medium used was yeast extract, dextrose and either cobalt carbonate or cobaltous ammonium lactate. The medium contained 2.0% yeast extract, 5.0% dextrose and either 0.001%–0.03% cobalt carbonate or 0.001%–0.03% cobalt carbonate equivalent in cobaltous ammonium lactate. All ingredients were added on a weight-to-volume basis. The culture medium was sterilized for 15 minutes at 15 PSIG steam. Serial transfer culturing was carried out as described in Example 1. Typical response to the presence of cobalt is shown in the tables below. The responses are not limited to only these cobalt concentrations.

TABLE 1

*Streptococcus faecium* Growth in Cobalt Free Yeast Extract Glucose Medium.

| Number of Serial Transfers | Titratable Acidity (%) | Cell Count Acid Dilutions | Cell Count Base Dilutions | Amount (%) Declumping |
|---|---|---|---|---|
| 1 | 0.8 | 18 | 18 | 0 |
| 2 | 0.8 | 19 | 19 | 0 |
| 3 | 0.9 | 19 | 22 | 16 |
| 4 | 1.1 | 21 | 40 | 90 |
| 5 | 1.3 | 32 | 80 | 150 |

TABLE 2

*Streptococcus faecium* Growth in Cobalt Carbonate Yeast Extract Dextrose Medium.

| Number of Serial Transfers | Titratable Acidity (%) | Cell Count Acid Dilutions | Cell Count Base Dilutions | Amount (%) Declumping |
|---|---|---|---|---|
| 1 | 0.9 | 16 | 19 | 19 |
| 2 | 1.1 | 19 | 26 | 37 |
| 3 | 1.1 | 19 | 28 | 47 |
| 4 | 1.3 | 24 | 50 | 108 |
| 5 | 1.3 | 45 | 516 | 596 |

TABLE 3

*Streptococcus faecium* Growth in Cobaltous Ammonium Lactate Yeast Extract Dextrose Medium.

| Number of Serial Transfers | Titratable Acidity (%) | Cell Count Acid Dilutions | Cell Count Base Dilutions | Amount (%) Declumping |
|---|---|---|---|---|
| 1 | 0.9 | 25 | 25 | 0 |
| 2 | 1.2 | 28 | 28 | 0 |
| 3 | 1.3 | 35 | 36 | 3 |
| 4 | 1.7 | 91 | 99 | 9 |
| 5 | 2.0 | 140 | 160 | 14 |

EXAMPLE 9

In this example *Streptococcus faecium* ATCC strain No. 19434 was used. The culture medium used was fish meal, dextrose and either cobalt carbonate or cobaltous ammonium lactate. The fish meal medium was prepared as described in Example 3. Serial culturing of *Streptococcus faecium* was done according to the procedure in Example 1. Typical response to the presence of cobalt is shown in the results obtained. The responses are not limited to only these cobalt concentrations.

EXAMPLE 10

In this example *Streptococcus faecium* ATCC strain No. 19434 was used. The culture medium used was skim milk and either cobalt carbonate or cobaltous ammonium lactate. The medium preparation, inoculation and culture serial transfers were performed according to procedures described in Examples 2 and 1, respectively. Typical responses to growth in the presence are observed in presence and absence of cobalt. These data are not to be considered the only cultural conditions test, rather examples of responses found.

EXAMPLE II

The sub-culture product of organisms treated in the presence of the metallic ion and rendered non-clumping by the teachings of this invention are then fermented in production steps using the metallic ion and nutrients in the manner set forth in my U.S. Pat. No. 3,497,359, for example, with a final stabilizing step to render the organisms non-viable. The resulting production process is more efficient because of the higher acidity, higher density of bacteria growth and the improved nutrition during the production steps afforded by the non-clumping organism characteristic.

The various organisms of the Examples exemplify those which exhibit the characteristic of enhancing the culture of living animal and plant growth when administered in small quantities in the non-viable state.

Having therefore advanced the state of the art by producing improved processes for producing organisms and resulting organism products which are active in the enhancement of living animal and plant growth, those novel features believed descriptive of the nature and spirit of the invention are defined with particularly in the appended claims.

I claim:

1. The improved process of producing non-clumping organisms of the class including Lactobacillus and Streptococcus cultured in the presence of cobalt carbonate to develop characteristics which enhance plant and animal growth when administered in small quantities, comprising the steps of, selecting a strain of said organisms that when cultured in the presence of said cobalt carbonate will become active in the enhancement of living animal and plant growth but which when subjected to the cobalt carbonate in culture in a nutrient medium develops the characteristic of clumping and a limitation on the percentage of acidity tolerated, sub-culturing said strain through a series of as many culture steps each in a fresh medium containing the cobalt carbonate and ammonium lactate as required to develop a non-clumping organism, producing a product by fermentation of the non-clumping organism in the presence of the cobalt carbonate and nutrients with an acidity higher than said limitation thereby increasing the production efficiency.

2. The process defined in claim 1 including the production step of rendering the organism non-viable by significantly increasing the acidity to produce the organism in non-viable form.

3. The process defined in claim 1 wherein the organism is *Lactobacillus bulgaricus.*

4. The process defined in claim 1 wherein the organism is a Streptococcus strain.

5. The process defined in claim 1 wherein the organism is Streptococcus faecium.

6. The process defined in claim 1 wherein the organism is *Lactobacillus plantarum.*

7. The process defined in claim 1 wherein the nutrient medium comprises corn steep liquor.

8. The process defined in claim 1 wherein the nutrient medium comprises yeast extract.

9. The process defined in claim 1 wherein the organism is *Lactobacillus casei* and the nutrient medium is milk.

* * * * *